US007600873B2

(12) United States Patent
Grundig

(10) Patent No.: US 7,600,873 B2
(45) Date of Patent: Oct. 13, 2009

(54) METHOD OF DETERMINING THE SPATIAL RELATIONSHIP OF AN EYE OF A PERSON WITH RESPECT TO A CAMERA DEVICE

(75) Inventor: Martin Grundig, Rangsdorf (DE)

(73) Assignee: SensoMotoric Instruments GmbH, Teltow (DE)

( * ) Notice: Subject to any disclaimer, the term of this patent is extended or adjusted under 35 U.S.C. 154(b) by 347 days.

(21) Appl. No.: 11/621,899

(22) Filed: Jan. 10, 2007

(65) Prior Publication Data

US 2007/0171369 A1 Jul. 26, 2007

(30) Foreign Application Priority Data

Jan. 16, 2006 (DE) ........................ 10 2006 002 001

(51) Int. Cl.
*A61B 3/14* (2006.01)
*A61B 3/00* (2006.01)
(52) U.S. Cl. ........................ 351/210; 351/246
(58) Field of Classification Search ................ 351/205, 351/209–210, 246
See application file for complete search history.

(56) References Cited

U.S. PATENT DOCUMENTS 5,583,795 A 12/1996 Smyth 6,659,611 B2 * 12/2003 Amir et al. .................. 351/210
2003/0146901 A1 8/2003 Ryan
2006/0239670 A1 * 10/2006 Cleveland .................... 396/51

FOREIGN PATENT DOCUMENTS

DE 102005025462 2/2006

OTHER PUBLICATIONS

Jenwen Wu u. Mohan M. Trivedi: A Binary Tree for Probability Learning ni Eye Detection. In: Proceedings of the 2005 IEEE Computer Society on Computer Society on Computer Vision and Pattern Recognition (CVPR'05), 2005, S. 1-8.
Steifelhagen, Rainer U.A.: A Model-Based Gaze Tracking System. In: IEEE Internat. Joint Symposia on Intelligence and Systems, Nov. 4-5, 1996, S. 304-310.

* cited by examiner

*Primary Examiner*—Scott J Sugarman
*Assistant Examiner*—Dawayne A Pinkney
(74) *Attorney, Agent, or Firm*—Marger Johnson & McCollom, P.C.

(57) ABSTRACT

A method of determining the spatial relationship of an eye (10) of a person with respect to a camera device (20) which provides images of the eye (10) comprises:
a model acquisition phase in which a customized model of the eye (10) is constructed and a reference spatial relationship of the eye model with respect to the camera device (20) is determined using a reference image of the eye (10); and
a tracking phase in which position and/or rotation coordinates of the eye (10) are determined by aligning the eye model to a current image of the eye (10).

21 Claims, 14 Drawing Sheets

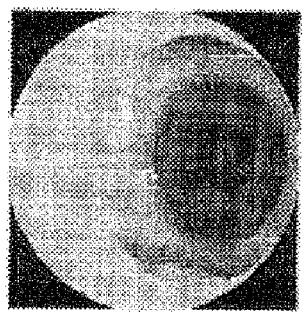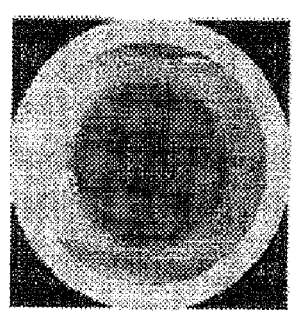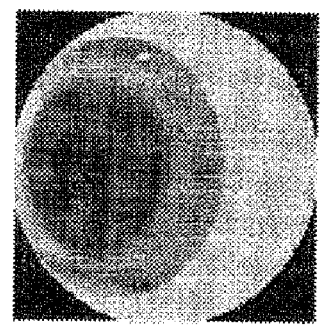
Fig. 11

METHOD OF DETERMINING THE SPATIAL RELATIONSHIP OF AN EYE OF A PERSON WITH RESPECT TO A CAMERA DEVICE

BACKGROUND OF THE INVENTION

The present invention refers to a method of determining the spatial relationship of an eye of a person with respect to a camera device which provides images of the eye.

More particularly, the invention refers to a model based technique for eye tracking using a single camera, in particular a single digital camera. Eye tracking applications are numerous and range from gaze tracking, i.e. analyzing which object a person is looking at for marketing studies, research in neuroscience or military applications to eye tracking in medical applications.

The present invention has potential in a number of eye tracking applications, with the largest relevance in the field of medical eye tracking during corneal ablation surgery.

The term "eye tracking" usually refers to the repeated or even continuous estimation of eye movements of a person. However, in the context of the present invention, this term may also be used for a single determination of the spatial relationship of the person's eye with respect to the camera device based on the current eye image.

As in prior art methods of determining the spatial relationship of a person's eye with respect to a camera device, the present invention is based on the assumption that the eye has six degrees of freedom to move in three-dimensional space, namely three translations defining the eye's position as well as three rotations defining the eye's orientation, as is illustrated in FIG. 1.

Some eye tracking systems use head mounted cameras or a camera attached to a head rest or a chin rest. In this special case all eye movements with respect to the camera can be interpreted as rotations and after calibration the line of sight can be recovered by detecting the pupil in the camera image. These systems are intrusive and uncomfortable though and require the use of a headrest, a chin rest or a helmet.

Standard non-intrusive techniques detect the pupil in the camera image together with corneal reflexes (so called 1st purkinje images) caused by illumination sources at a defined position relative to the camera. When using at least two illumination sources it is possible to recover five degrees of freedom of the eye, three translations and two rotations. Alternatively some approaches not only use corneal reflections but also reflections from the eye's lense. All these reflections of refractive surfaces are called purkinje images. It is not possible to recover the rotation around the symmetry axis of the eye using purkinje images. These techniques are used for gaze tracking in different applications and are usually referred to as purkinje approaches.

Other non-intrusive techniques for eye tracking using one digital camera simply detect the pupil in the 2D camera image. With this information it is not possible to distinguish between eye rotation and eye translation. Systems like this are often employed in ophthalmic treatment lasers for corneal ablation. These systems track the pupil but the ablation is performed on the cornea which is located appr. 3 mm in front of the pupil. Systematic ablation errors do occur if large eye rotations happen during surgery since they are solely interpreted as translations (or vice versa). The detection of corneal reflections to be able to distinguish between eye rotation and eye translation is not possible in this application, because in the standard procedure for corneal ablation (LASIK) a thin layer of the cornea having a thickness of approximately 180 microns is cut off. The cornea surface is not smooth anymore and corneal reflections can not be localised accurately. This is illustrated in FIGS. 2a and 2b showing purkinje images of a person's eye before and after the thin cornea layer has been cut of, respectively. In FIG. 2a, the cornea of the person is intact, so that the corneal reflexes of two illumination sources located at a defined position in space can be accurately detected. The cornea surface in this case acts more or less like a mirror. In FIG. 2b, however, the same eye is shown after a flap cut. The cornea surface is not smooth anymore and corneal reflexes can no longer be detected. The standard purkinje approach to determine the position of the eye as well as two among the three rotation coordinates can therefore no longer be used.

It is therefore an object of the invention to provide a method of determining the spatial relationship of an eye of a person with respect to a camera device which does not rely on corneal reflections, which is less intrusive and uncomfortable than the above-discussed prior art tracking methods, and which allows to recover all eye movements in six degrees of freedom.

SUMMARY OF THE INVENTION

According to the invention this object is achieved by a method of determining the spatial relationship of an eye of a person with respect to a camera device which provides images of the eye which comprises:
- a model acquisition phase in which a customized model of the eye is constructed and a reference spatial relationship of the eye model with respect to the camera device is determined using a reference image of the eye; and
- a tracking phase in which position and/or rotation coordinates of the eye are determined by aligning the eye model to a current image of the eye.

The model acquisition phase corresponds to a kind of initial setup phase in which the eye's reference image is taken by the camera device and analyzed by a computer such as to determine the reference spatial relationship of the eye model which represents the person's eye with respect to the camera device.

Later on, namely during the tracking phase, the current position and/or rotation coordinates of the eye can be determined by aligning the eye model which has been initialized during the model acquisition phase to the current eye image as provided by the camera device. This alignment is usually accomplished by numerical fitting algorithms conducted by the computer.

Preferably the eye model comprises:
- a three-dimensional eye shape model representing the surface of the eye and being aligned with the reference image of the eye during the model acquisition phase; and
- texture information associated with a plurality of points located on the surface of the eye.

Aligning the eye shape model with the reference image of the eye can then efficiently be accomplished by numerically fitting the eye's translation and/or rotation coordinates.

In a simple embodiment, the three-dimensional eye shape model comprises a superposition of two ellipsoids, one of which represents the globe and the other of which represents the cornea. The pupil is then usually supposed to lie in the sectional plane of the two ellipsoids.

This embodiment can still further be simplified by assuming that at least one of the two ellipsoids is a sphere.

In alternative embodiments, the three-dimensional eye shape model may comprise a wire mesh structure of connected points, or may comprise a plurality of points defined by linear combinations of shape eigenvectors.

Several possibilities may be envisaged for determining the reference spatial relationship of the eye model with respect to the camera device during the model acquisition phase:

In the preferred embodiment of the invention, the reference spatial relationship of the eye shape model with respect to the camera device is obtained by applying a purkinje analysis to the reference image of the eye based on corneal reflexes of illumination sources located at predefined positions relative to the camera device. As has been discussed above, this purkinje approach allows to precisely measure the three translation coordinates and two rotation coordinates of the eye before an eventual cornea flap cut.

The "missing" rotation coordinate, namely the angle of rotation of the eye about its symmetry axis, can not be measured on an absolute scale. However, as eye tracking is rather interested in measuring eye movements with respect to an initial position, it is sufficient to simply define the coordinate of eye rotation about the eye's symmetry axis as zero degrees in the reference image.

In a less time-consuming embodiment the above purkinje analysis for determining the reference spatial relationship of the eye shape model with respect to the camera device may be replaced by an assumption that the person is fixating at a fixed position in space previously defined relative to the camera device. In other words, a reference image of the eye is taken during the model acquisition phase, and the eye's rotation coordinates are supposed to be known because the person has been previously instructed to fixate at a specific point in space. For example, the person may have been instructed to look into the camera device during the model acquisition phase, which means that all eye angles can be defined as zero degrees. Furthermore the distance of the eye from the camera device is usually known during the model acquisition phase, so that only two translation coordinates in a plane normal to the eye's symmetry axis remain to be determined with respect to the camera device based on the reference eye image.

In the preferred embodiment of the invention, the texture information is stored as a feature template map comprising:
- three-dimensional model coordinates of a plurality of reference image points at which eye features are located; and
- templates containing parts of the reference image extracted around each associated point and showing the corresponding eye feature.

More specifically these eye features may be selected from the group consisting of blood vessels, iris features, limbus, limbus centre, pupil centre, pupil edge and artificial markers.

Thus, during the model acquisition phase an operator may watch the reference image of the person's eye and select characteristic features like for example blood vessels, the pupil edge etc. For example, the operator may select an eye feature in the reference image by clicking thereon with a computer mouse device. Preferably, however, the characteristic features are automatically selected by the computer by determining features in the reference image having a large gray value gradient in two dimensions, which are therefore well suited for tracking purposes. The three-dimensional model coordinates of each such image point are stored together with the associated template which corresponds to an image of the feature extracted from the full reference image.

Advantageously, the three-dimensional model coordinates of a point are obtained by detecting the corresponding eye feature in the reference image of the eye and intersecting a projecting ray of the eye feature with the aligned eye shape model. The computer then calculates the corresponding projecting ray, i.e. the line starting from the selected point and passing through the projection centre of the camera device, and determines a point of intersection of the projecting ray with the eye shape model that has been previously aligned during the model acquisition phase. This method allows to calculate the three-dimensional model coordinates of each characteristic feature which has been selected in the two-dimensional reference image, which three-dimensional coordinates are then stored in the feature template map together with the associated feature template.

In this embodiment in which a feature template map is used, the tracking phase may preferably comprise the following steps:
a) a template matching step in which for a plurality of feature templates stored in the feature template map, a region in the current eye image bearing the largest resemblance to the respective feature template is searched;
b) a coordinate determination step in which the coordinates of the regions found in step a) are determined as respective current feature positions; and
c) an alignment step in which an image distance between the current feature positions determined in step b) and the positions of the corresponding three-dimensional model features projected into the current eye image is minimized by fitting orientation and/or rotation parameters of the eye model.

All steps of the tracking phase will advantageously be conducted numerically by the same computer controlling the model acquisition phase.

Although template matching is a standard tool in modern digital image analysis, it may nevertheless be helpful to reduce the search time required to find a feature template in the current eye image. Therefore, for each feature template stored in the feature template map, the search conducted during the template matching step should be limited to a predefined zone of the current eye image around the feature position determined in a previous coordinate determination step. This previous coordinate determination step may be the initial coordinate determination step conducted during the model acquisition phase based on the reference image. In other words, when template matching is accomplished for the first time during the tracking phase, the search for the region in the current eye image bearing the largest resemblance to the feature template may be limited to a predefined zone of the current eye image next to the initial feature position as measured in the reference image.

The texture information stored as part of the eye model need not necessarily be provided as a feature template map. Instead, an alternative embodiment may be envisaged in which the texture information is stored as a gray value map comprising:
- three-dimensional model coordinates of a plurality of previously defined reference image points; and
- gray values extracted from the reference image at each of the points.

Also in this alternative embodiment, the three-dimensional model coordinates of a point are obtained by intersecting a projecting ray of the reference image point with the aligned eye shape model.

Contrary to the above-discussed first embodiment using a feature template map, the previously defined reference image points used in the gray value map embodiment need not be individually selected by the computer or by an operator based on an analysis of the eye's reference image. Instead a large number of previously defined reference image points is usually automatically selected from the reference image, their three-dimensional model coordinates are calculated by the above-discussed intersection method, and each set of three-dimensional model coordinates of a point is stored together with the corresponding gray value of the reference image at this point in the gray value map.

In this embodiment, the tracking phase comprises an alignment step in which the total gray value difference between the current eye image and the gray value map projected into the current eye image is minimized by fitting orientation and/or rotation parameters of the eye model.

In all embodiments of the invention it is theoretically possible to track the person's eye only once, for example in gaze tracking applications in market studies. It may for example be interesting to find out in which direction a client looks first after having entered a shop.

However, especially in corneal ablation surgery it is preferred that the tracking phase is continuously repeated in regular time intervals.

In these medical applications, the method according to the invention furthermore comprises a step of determining a spatial relationship of the person's eye with respect to a surgical device based on a previously determined spatial relationship of the camera device with respect to the surgical device. The surgical device may in particular be a laser used for corneal ablation. The method according to the invention then allows to continuously provide the current position and rotation coordinates of the patient's eye. The laser may then automatically be moved in order to compensate for the undesired eye movements such as to make sure that the laser beam always hits the patient's cornea at the correct position.

In all embodiments of the method according to the invention, the spatial tracking phase may furthermore comprise determining internal degrees of freedom of the eye model selected from the group consisting of relative movements of eye model features, scaling of the whole eye model, scaling of eye model features, deformations of the whole eye model, deformations of eye model features and appearance changes due to illumination influences. A correspondingly improved numerical fitting algorithm allows to cope with changes in the current eye image with respect to the reference image which are not due to eye translations or rotations and will therefore improve the alignment results.

The invention furthermore refers to a computer program, comprising: computer program code which, when executed on a computer connected to a camera device, enables the computer to carry out a method according to any of the preceding claims.

BRIEF DESCRIPTION OF THE DRAWINGS

Other objects, characteristics and results of the invention will be clear from the following description given by way of non-limitative example and illustrated by the accompanying figures, in which:

FIG. 11 shows three gray value maps used in the second embodiment of the invention;

FIG. 1 is a schematic representation of a persons eye 10 and a coordinate system attached thereto. The z' axis of the coordinate system coincides with the eye's symmetry axis and thus passes through the eyeball 12, the lense 14 and the eyes cornea 16. In a plane perpendicular to the z' axis, two orthogonal coordinate axes x' and y', respectively are shown in FIG. 1.

Rotations about the x', y' and z' axis are defined by angles α', β' and γ', respectively.

Figure 1:
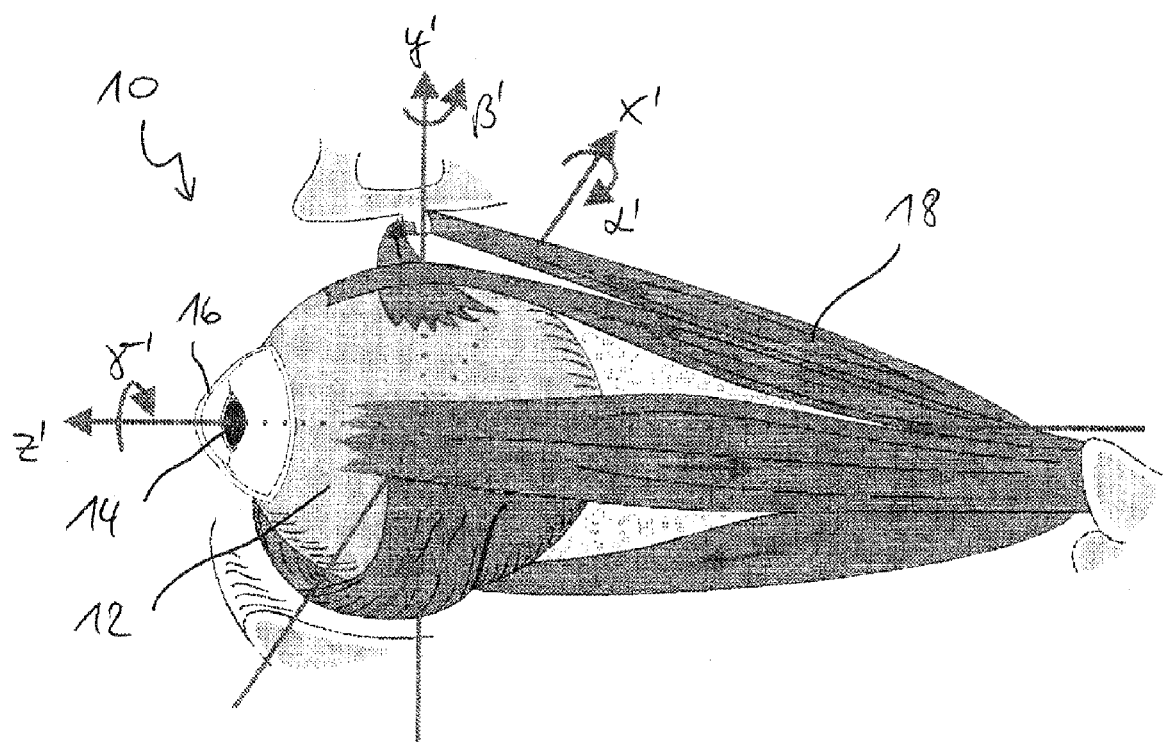
FIG. 1 is a schematic illustration of a human eye and a coordinate system attached thereto.

Furthermore various muscles 18 attached to the eyeball 12 are shown in FIG. 1. Intentional activities of these muscles 18 lead to eye translations and/or rotations, for example when the person intentionally looks at a certain object. On the other hand, unintentional activities of the muscles 18 may lead to translations and/or rotations of the eye 10 even when any such movement should be avoided, for example during eye surgery. In all these cases the method according to the invention allows to track the person's eye 10, i.e. to determine its current spatial relationship with respect to a camera device 20 which provides images of the eye 10, for example during corneal ablation surgery. A corresponding experimental setup is schematically shown in FIG. 3.

Figure 3:
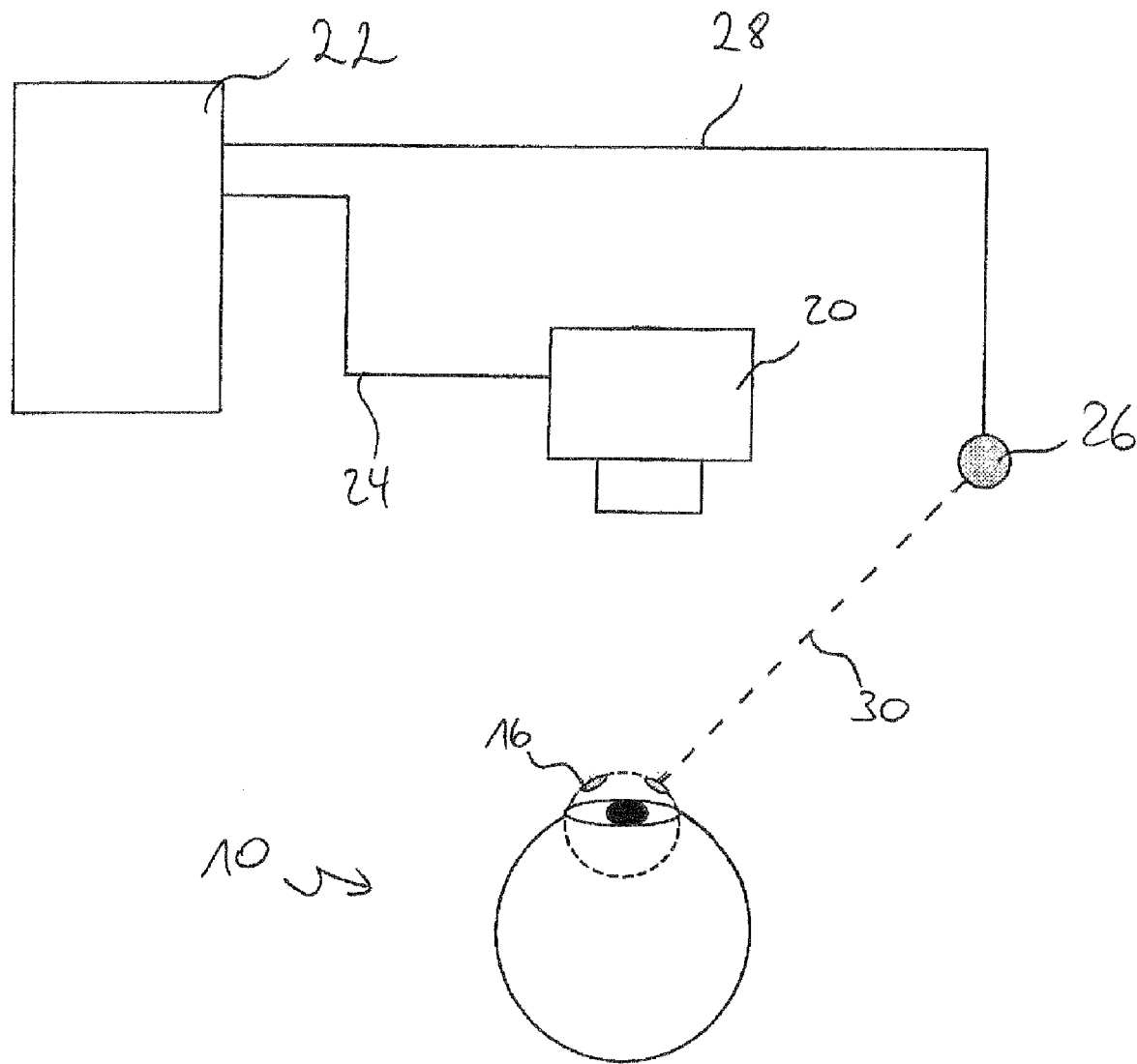
FIG. 3 is a schematic view illustrating an experimental setup used for corneal ablation surgery.
Figure 4:
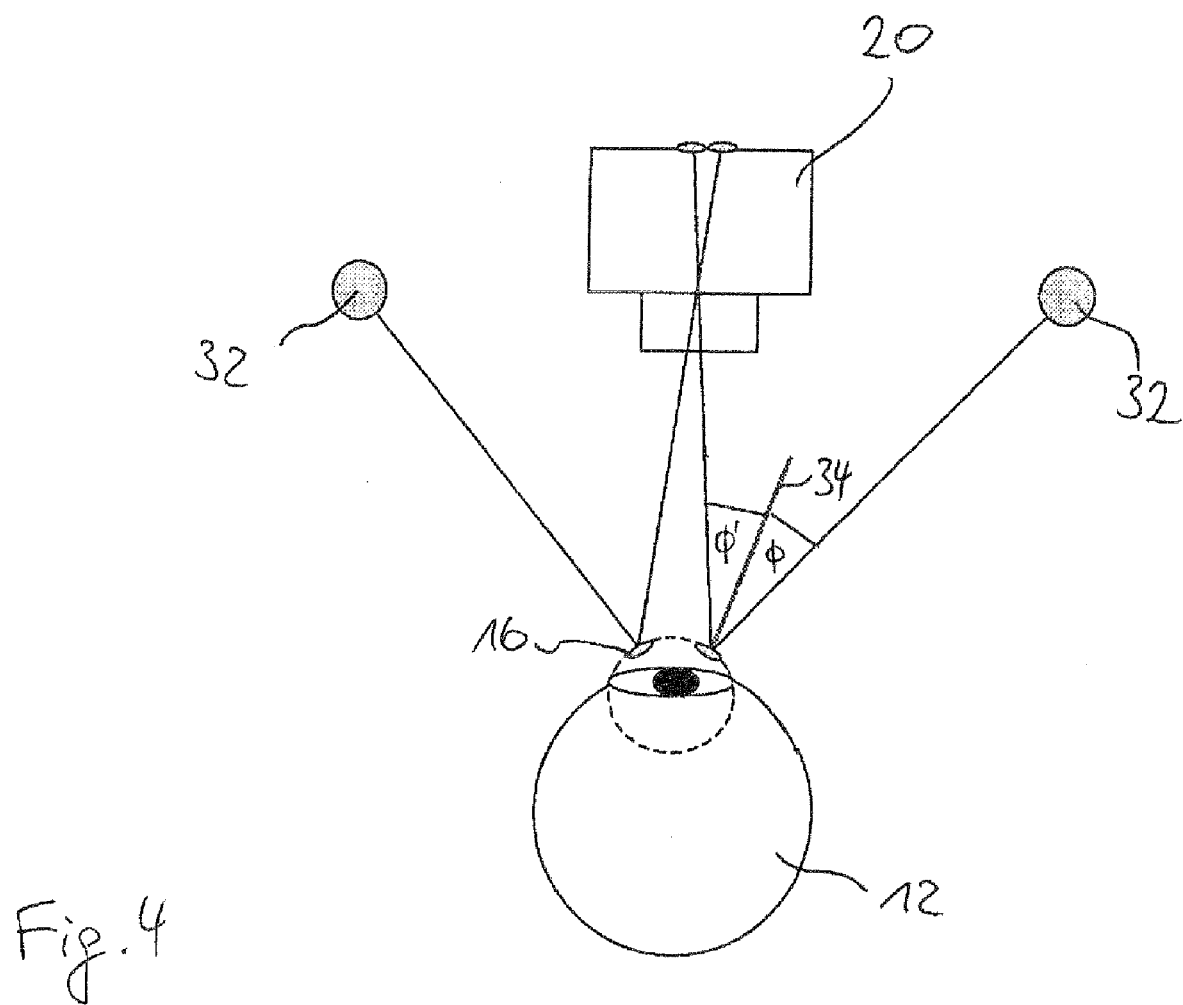
FIG. 4 shows a schematic experimental setup for purkinje analysis.
Figure 5:
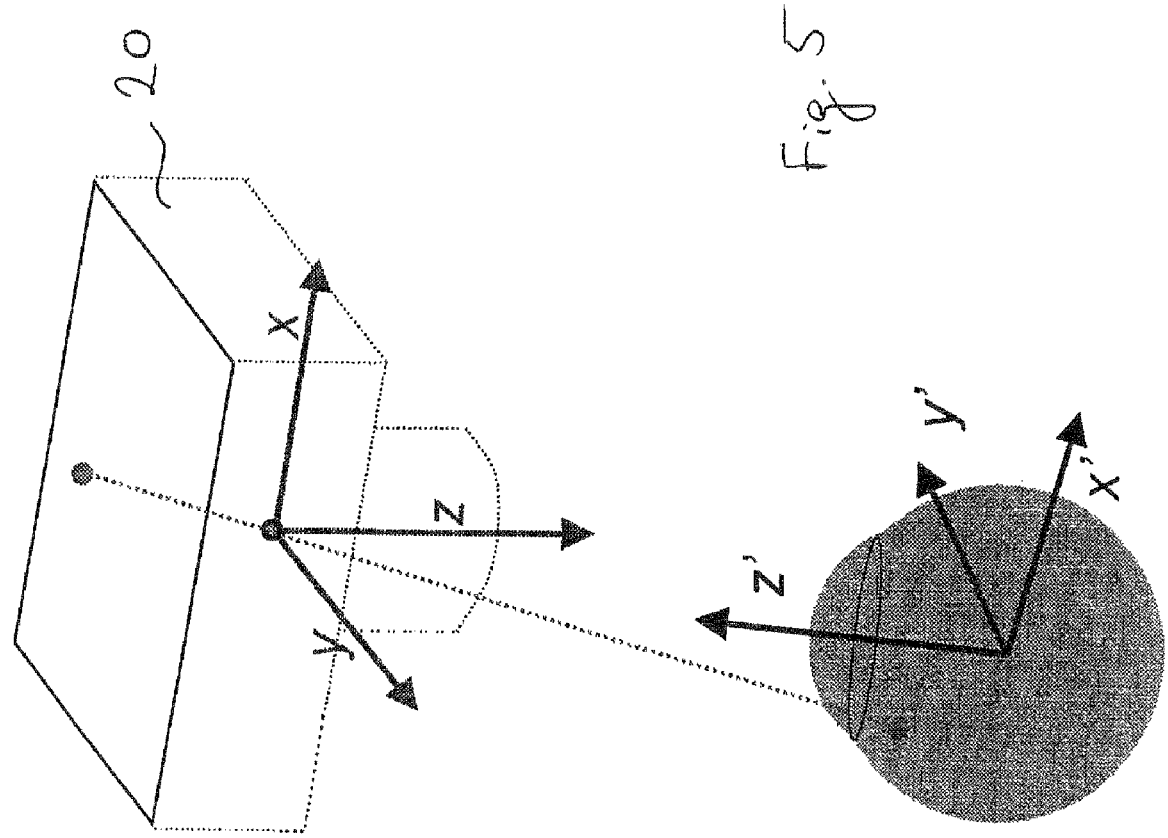
FIG. 5 is a schematic view illustrating the relationship between the person's eye having a coordinate system attached thereto and the camera device to which a main coordinate system fixed in space is attached.

In the typical surgical setup as shown in FIG. 3, a patient is positioned on a chair or a patient bed, and camera device 20 is arranged such as to face his eye 10 at a predefined distance.

The camera device 20 inputs the measured image data to a computer 22 via a data transmission line 24. The computer 22, in turn, controls a laser apparatus 26 via a control line 28. The laser apparatus 26 comprises a laser device and means for directing a laser beam emitted by the laser device to the cornea 16 for surgical purposes. Without any limitation, the means for directing the laser beam preferably comprise a plurality of individually adjustable mirrors which reflect the beam emitted from the laser device.

Alternatively the means for directing the laser beam could comprise an individually adjustable holder on which the laser device itself is mounted. Directing the laser beam is then accomplished by tilting or shifting the laser device itself.

The computer 22 executes computer program code allowing to carry out the method according to the invention in such a way that unintentional movements of the cornea 16 are tracked via the camera device 20, and suitable control signals are calculated by the computer 22 and sent to the laser apparatus 26 via the control line 28 such as to automatically shift the laser beam 30 emitted by the laser apparatus 26 in an appropriate way. Thus, unintentional eye movements can be compensated for, and it can be made sure that the laser beam 30 hits the cornea 16 at the desired spot. Alternatively, instead of compensating for eye movements, the laser apparatus 26 can be switched off or the laser beam can be blocked when it is detected that the current eye orientation is not within an acceptable range.

Preferred embodiments of the method according to the invention as controlled by the computer 22 will now be described in detail in connection with FIGS. 4 to 14.

When the camera device 20 has been positioned in front of the patient's eye 10, the model acquisition phase of the method according to the invention is started in which a customized model of the eye 10 is constructed and the reference spatial relationship of the eye model with respect to the camera device 20 is determined. The customized eye model comprises a three-dimensional eye shape model representing the surface of the eye 10. In the embodiment shown in FIG. 4, this eye shape model corresponds to a superposition of two spheres: the eyeball or globe 12 is represented by the larger sphere shown in FIG. 4, whereas the cornea 16 is represented by the part of a smaller sphere shown in dotted lines and projecting from the globe 12 in the direction of the camera device 20. The radius of the larger sphere and the smaller sphere, respectively, is assumed to be known.

At the beginning of the model acquisition phase, the x, y, and z position coordinates of the eye 10 as represented by the customized model as well as the rotation coordinates $\alpha$ and $\beta$ are calculated in the fixed coordinate system attached to the camera device 20 by a purkinje analysis which is generally known in the art:

To this end, the corneal reflexes of light beams emitted from two illumination sources 32 which are located at known positions relative to the camera device 20 are detected in the camera image. In addition the limbus or pupil center is also detected in the camera image. The calculation of the coordinates x, y, z, $\alpha$ and $\beta$ is based on an estimated distance between the limbus or pupil center and the center of the cornea 16. Furthermore it is assumed that the cornea 16 can not only be represented by the perfect sphere shown in dotted lines in FIG. 4, but that it is also a perfect reflector. Then for each light beam emitted by one of the illumination sources 32 and hitting the cornea 16, the exit angle $\phi'$ with respect to the local surface normal 34 can be supposed to equal the corresponding incident angle $\phi$.

Figure 2A:
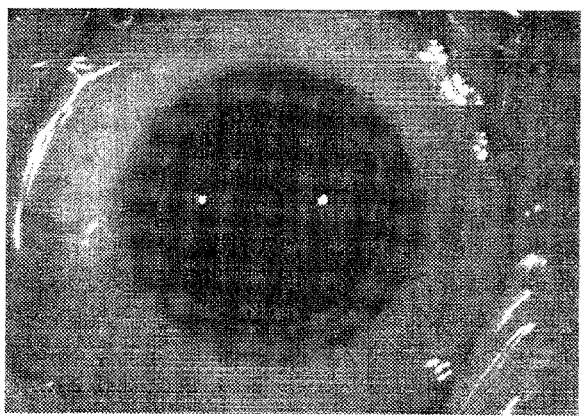
FIG. 2a is a photograph of a person's eye during a purkinje analysis, the cornea of the eye being intact.

FIG. 2a shows the corresponding light spots in the pupil of the eye 10, on which this purkinje method of aligning the eye shape model is based.

Figure 2B:
FIG. 2b is a photograph similar to FIG. 2a in the case of a cornea layer having been cut off.

Correspondingly, in the eye image of FIG. 2b where the same eye 10 is shown after a flap cut, corneal reflexes can no longer be detected, as the corneal surface is not smooth anymore. It is therefore essential that the model acquisition phase of the method according to the invention be accomplished before corneal ablation surgery is started.

When the initial purkinje step of the model acquisition phase is terminated, coordinates x, y, z, $\alpha$ and $\beta$ of the eye shape model have been calculated and are known in a coordinate system attached to the camera device.

Then as a next step during the model acquisition phase texture information about the eye is obtained and stored in computer 22 as a map associated to the eye surface represented by the eye shape model.

In the preferred embodiment discussed in connection with FIGS. 6 to 10, this map is a feature template map containing information about the position and structure of characteristic eye features. As particularly suitable features, blood vessels appearing in the eye image can be chosen, as is clear from FIG. 6 which shows an eye image taken by the camera device 20.

Figure 6:
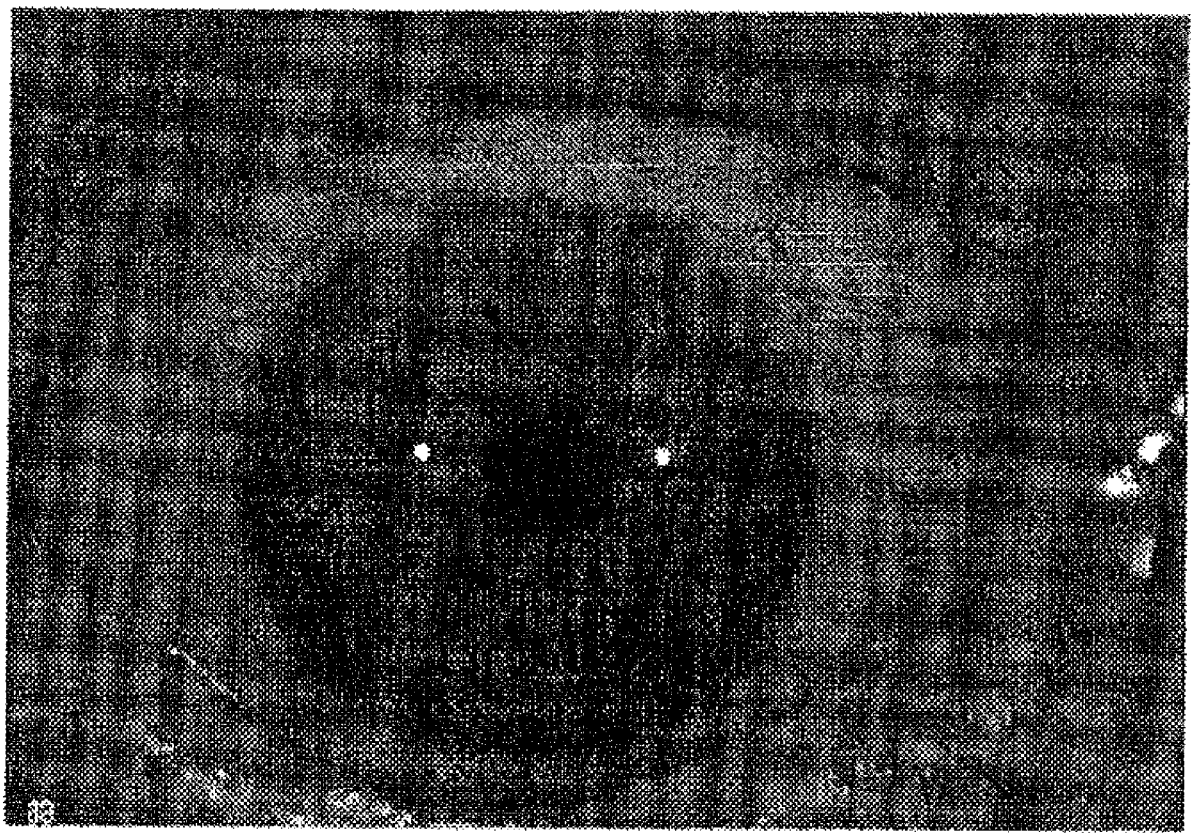
FIG. 6 is an enlarged image of a person's eye with characteristic blood vessel features.
Figure 7:
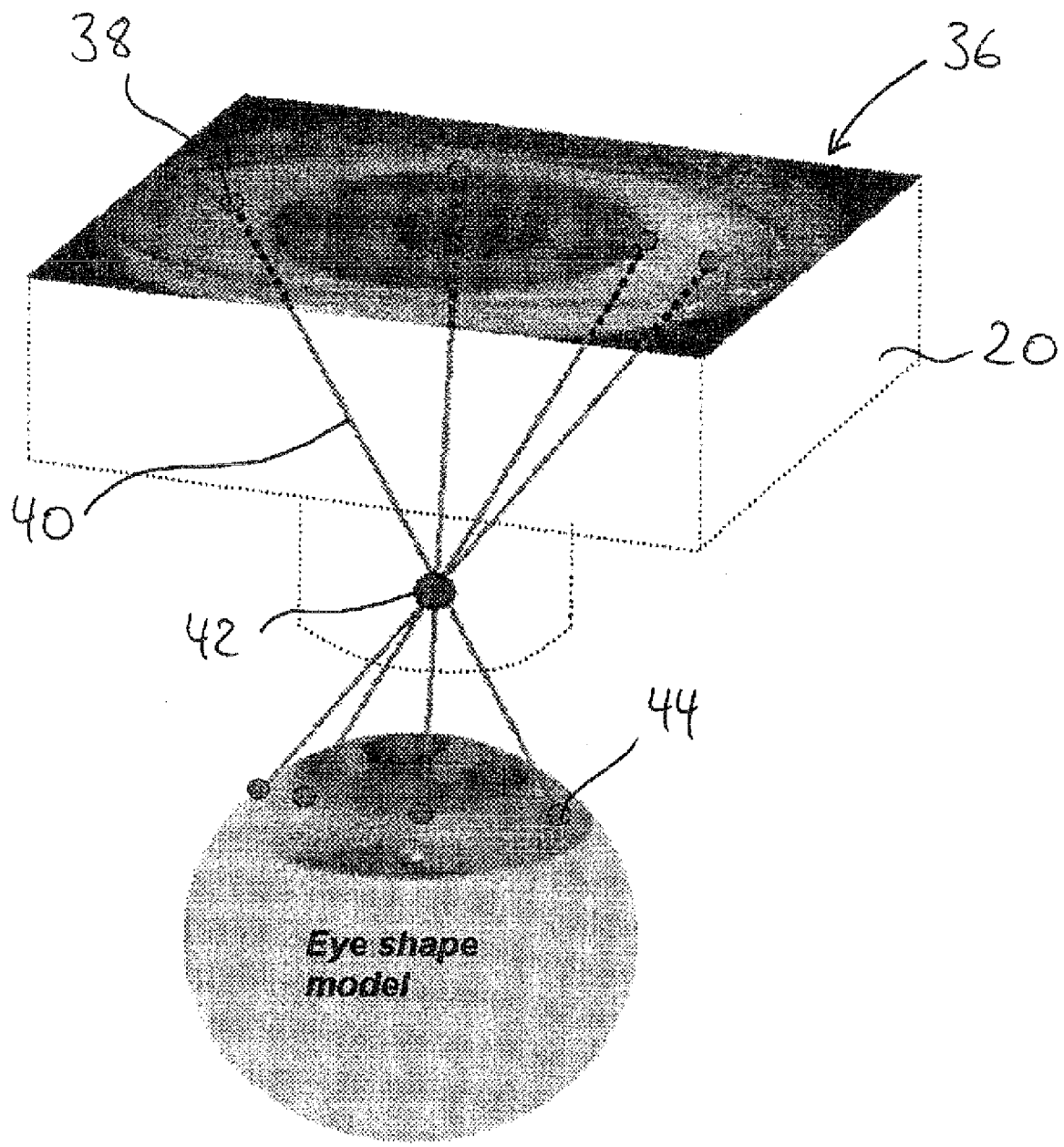
FIG. 7 is a schematic representation of projecting rays simulated by a computer during the model acquisition phase, according to a first embodiment of the invention.

More specifically, an operator takes a reference image of the person's eye 10, and then characteristic features like for example the blood vessels, the pupil edge etc. as clearly visible in FIG. 6 are selected in the way described above. This selection may be watched on a screen 36 on which the reference image is displayed. In FIG. 7, screen 36 is shown at the back of camera device 20 for simplicity reason. However, a separate screen 36 may be used which is connected to computer 22 and receives the reference image from the camera device 20 via data transmission line 24 and computer 22.

For each characteristic eye feature selected, computer 22 calculates a projecting ray, i.e. a line starting from the selected point and passing through the projection center of the camera device, whose position is a basic optical parameter of the camera device 20 and thus known. In FIG. 7, several selected characteristic points are shown, for example selected point 38, together with their corresponding projecting rays, for example ray 40, all of which pass through the camera's projection center 42.

Computer 22 then calculates the three-dimensional model coordinates x', y' and z' of each corresponding point where a projecting ray intersects the previously aligned eye shape model. In FIG. 7, for example, projecting ray 40 intersects the eye shape model at point 44, whose three-dimensional coordinates x', y', z' and x, y, z, respectively, can thus be calculated both in the coordinate system attached to the eye 10 (see FIGS. 1 and 5) and in the coordinate system attached to the camera device 20 as the eye shape model has been aligned beforehand, which allows to calculate coordinate transformation for each point of the eye shape model.

Figure 8:
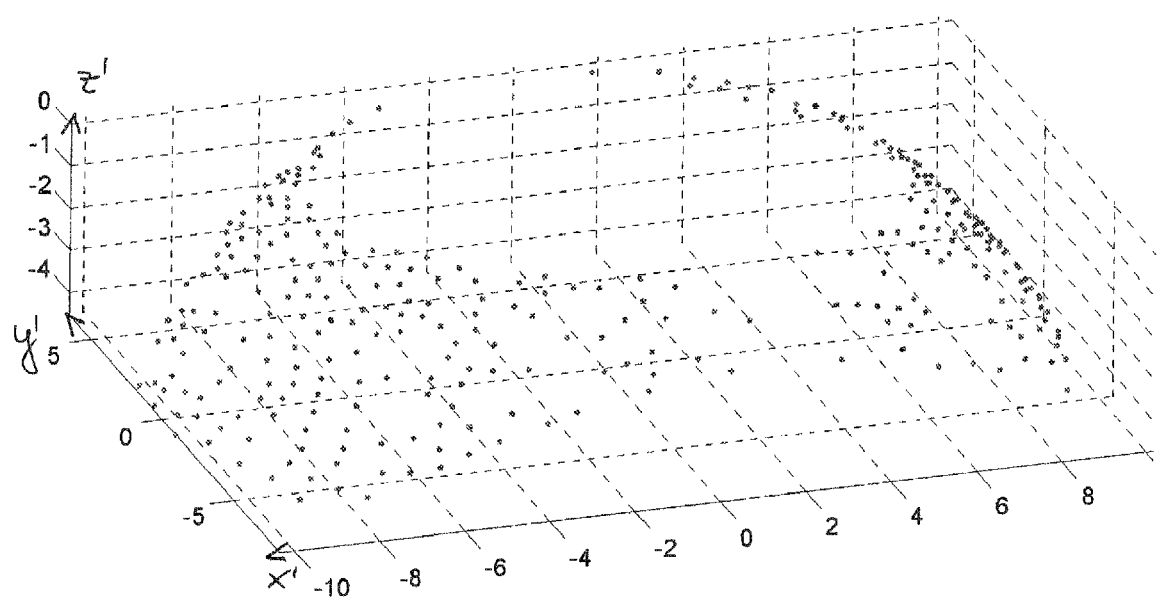
FIG. 8 shows the spatial distribution of reference image points in the coordinate system attached to the eye, according to the first embodiment of the invention.
Figure 9:
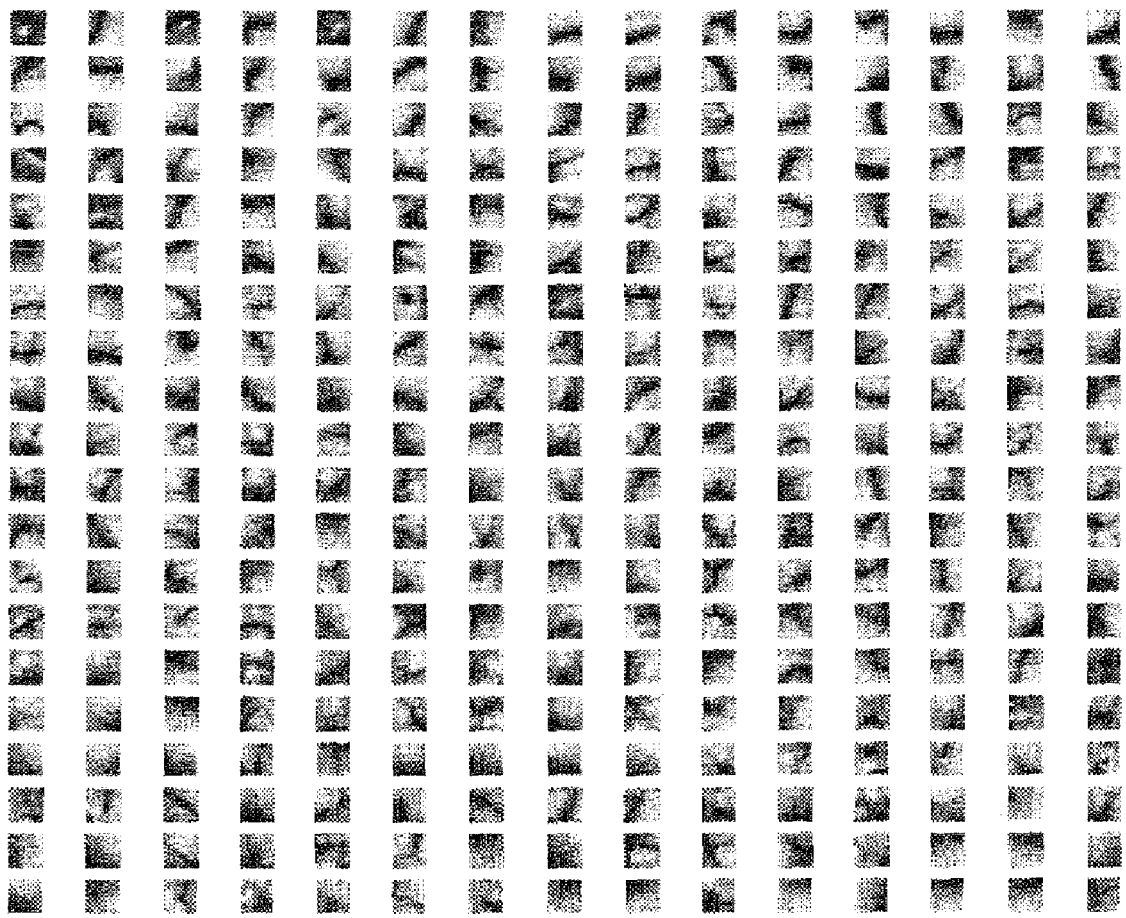
FIG. 9 shows a plurality of templates, each of which is associated to a respective reference image point, according to the first embodiment of the invention.

FIG. 8 represents a typical example of the correspondingly obtained locations of characteristic eye features on the surface of the aligned eye shape model. Each point depicted in the three-dimensional coordinate system of FIG. 8 corresponds to a characteristic eye feature and has been obtained by the above-described projecting ray intersection method. Furthermore computer 22 extracts a local image of each eye feature from the full reference image and stores it together with the three-dimensional model coordinates x', y' and z'. FIG. 9 shows a number of corresponding templates, each of which is associated to one of the points lying on the surface of the aligned eye shape model shown in FIG. 8.

As a result, at the end of the model acquisition phase computer 22 has calculated coordinates x, y, z, $\alpha$ and $\beta$ of the eye shape model in the coordinate system attached to the camera device 20, the "missing" rotation coordinate $\gamma$ being defined as zero degrees, and has furthermore determined three-dimensional model coordinates x', y' and z' of a plurality of characteristic eye features and stored them together with associated templates showing the structure of each respective feature.

Figure 10:
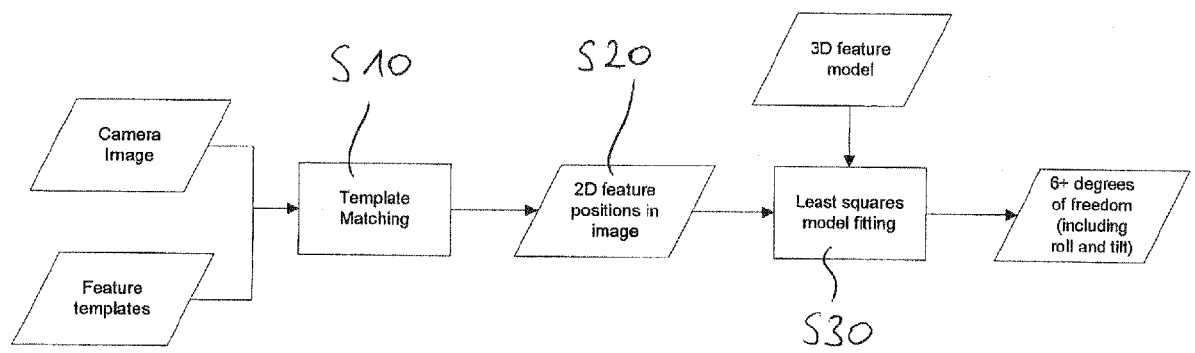
FIG. 10 is a schematic flow chart illustrating the method steps conducted in the first embodiment of the invention.

Based on these results of the model acquisition phase, the tracking phase of the preferred embodiment of the method according to the invention will now be explained in connection with FIG. 10.

At first computer 22 conducts a template matching step S10 based on the current image provided from camera device 20 and the feature template map stored in computer 22, e.g. on a hard disc installed therein. In the template matching step S10, one of the templates stored as part of the feature template map (see FIG. 9) is selected and the current image of the eye is searched for a region bearing the largest resemblance to the selected feature template. Such template matching methods which are for example based on normalized cross correlation algorithms are known in the art and will therefore not be explained in detail.

When the region bearing the largest resemblance to the selected feature template has been found in the current eye image, its position in terms of two-dimensional coordinates in the fixed coordinate system x, y, z is determined in a subsequent coordinate determination step S20 and temporarily stored in computer 22.

The template matching step S10 and the subsequent coordinate determination step S20 are conducted for a plurality of feature templates stored in computer 22 as part of the feature template map, preferably for all of its feature templates. Correspondingly, the two-dimensional feature positions are obtained in coordinate determination step S20 for said plurality of feature templates, and in the preferred case for all of the feature templates. The template matching step of the method according to the invention then proceeds to a subsequent alignment step S30, in which an image distance between the current feature positions determined in step S20 and the positions of the corresponding three-dimensional model features projected into the current eye image is minimized as follows:

The complete three-dimensional eye model which has been constructed and aligned with the reference image of the eye during the model acquisition phase is projected into the two-dimensional current eye image. For each feature template which has been matched during the template matching step S10 and whose two-dimensional coordinates in the current image have correspondingly been determined in the coordinate determination step S20, computer 22 then calculates the distance between its current position and the position of its projection. Calculating the sum of these distances for all feature templates yields the so-called image distance, which can be minimized by fitting orientation and/or rotation parameters of the eye model, for example by the well-known method of least squares fitting.

In other words, during alignment step S30 computer 22 analyses which translations and/or rotations of the eye model allow to reproduce the current eye image, and the characteristic eye features stored as the feature template map serve to "compare" the eye model and the current image.

As a result of alignment step S30 one therefore obtains three translation coordinates x, y and z as well as three rotation coordinates $\alpha$, $\beta$ and $\gamma$ describing the movement of the person's eye 10 in the fixed coordinate system with respect to its reference image. Based on the correspondingly obtained information, computer 22 may control laser apparatus 26 such as to compensate for the eye movements in order to make sure, that laser beam 30 hits the patients cornea 16 at the desired spot. Alternatively, as explained above, laser beam 30 may be switched off when the current eye orientation is found to be outside an acceptable orientation range.

The fitting algorithm used during alignment step S30 may possibly take further degrees of freedom of the eye 10 into account, for example relative movements of eye model features, scaling of the whole eye model, scaling of eye model features, deformations of the whole eye model, deformations of eye model features and appearance changes due to illumination influences.

Figure 12:
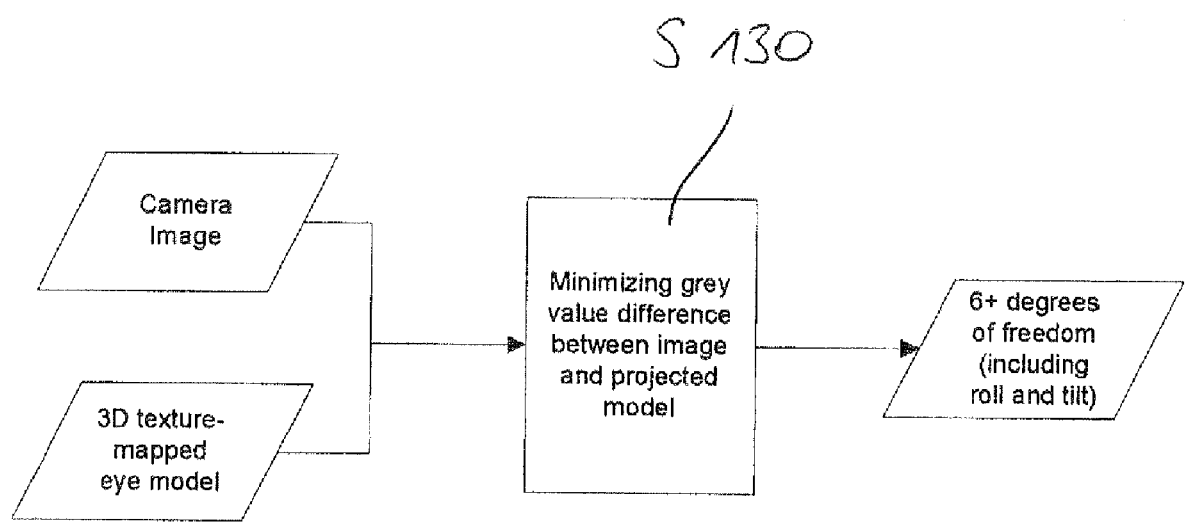
FIG. 12 is a schematic flow chart illustrating essential method steps of the second embodiment of the invention.

An alternative embodiment of the method according to the invention will now be described in connection with FIGS. 11 and 12.

In this alternative embodiment, the texture information of the eye model is stored as a gray value map derived from the reference image of the eye as obtained during the model acquisition phase. In this case there is no need to individually select characteristic eye features in the reference image as shown on a screen. Instead a large number of reference image points lying in the observation field of the camera device 20 has been previously defined on programming the computer program which allows to execute the method according to the invention. Then, when the reference image is taken by the camera device during the model acquisition phase, computer 22 calculates the three-dimensional model coordinates x', y', z' associated with each of the previously defined reference image points based on the above-explained intersection method, and furthermore determines the gray value of the reference image at each of the previously defined reference image points. The three-dimensional model coordinates x', y', z' of the reference image points as well as their respective gray values are then stored as a gray value map.

The number of previously defined points used for this alternative embodiment of the method according to the invention usually largely exceeds the number of points individually selected during the above discussed embodiment which is based on feature templates. In the illustrative case of FIGS. 8 and 9, for example, a total of 300 characteristic points have been individually selected by computer 22 based on the above-explained determination of gray value gradients in two dimensions in the reference image of the eye. In the gray value map embodiment, however, several thousands of regularly spaced points are usually previously defined and analyzed.

FIG. 11 shows three different views of a three-dimensional gray value map obtained from the reference image of the eye 10 and projected onto a screen. The three cases illustrated in FIG. 11 could for example correspond to three different rotation angles $\beta$ of the eye model (see FIG. 1), the middle image in FIG. 11 corresponding to the case $\beta=0$, i.e. the eye model corresponds to a person's eye 10 fixating at the camera device 20.

Figure 13:
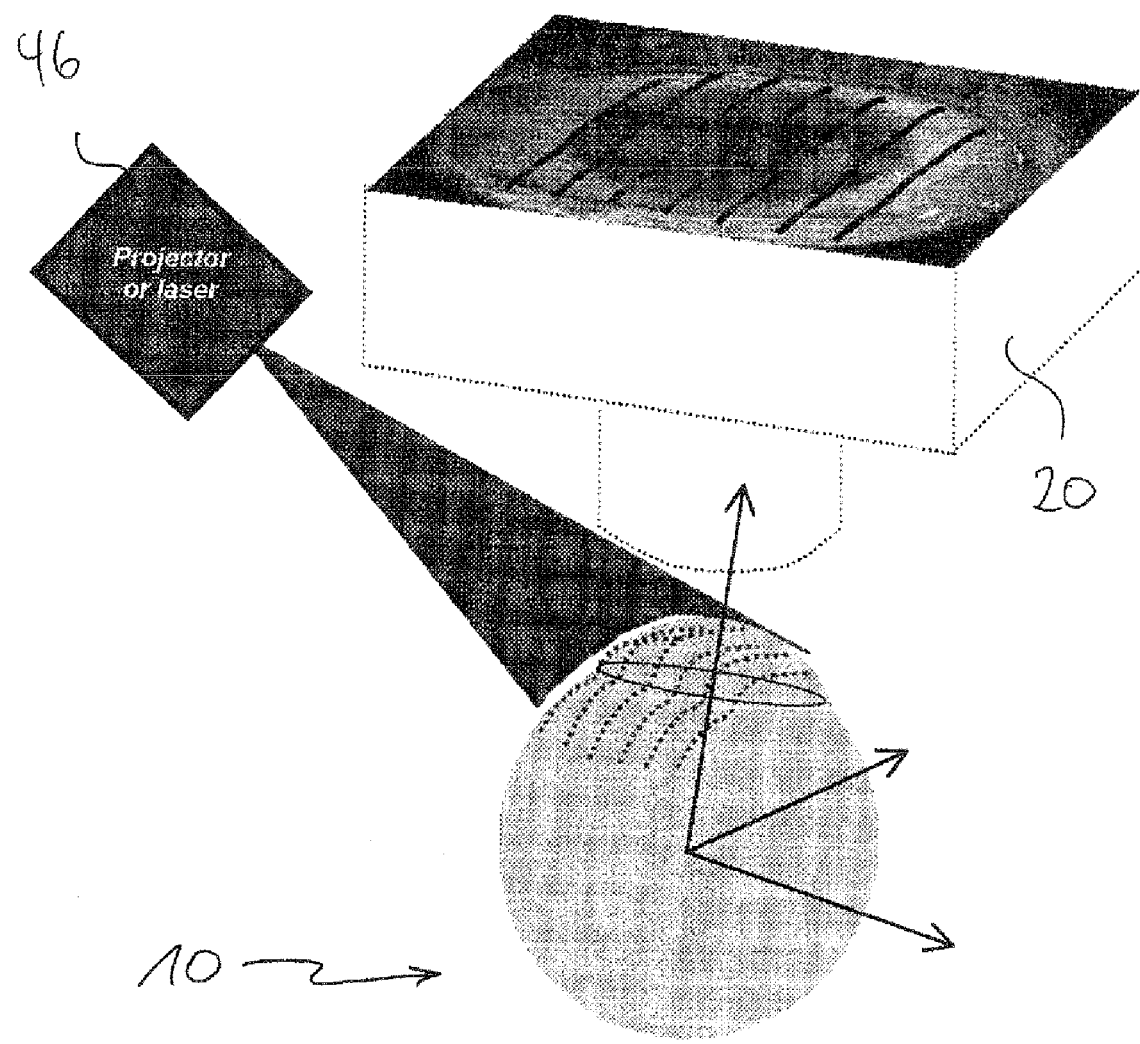
FIG. 13 shows an experimental setup used in an alternative embodiment of the invention based on eye model acquisition by triangulation of eye surface points.

In this alternative embodiment of the method according to the invention, the tracking phase as schematically illustrated by the flow chart in FIG. 13 comprises an alignment step S130 in which the total gray value difference between the current eye image and the gray value map projected into the current eye image is minimized as follows:

At first the three-dimensional gray value map is projected into the current eye image. Then, for a plurality of previously defined reference image points, preferably for all of the previously defined reference image points, computer 22 calculates the difference between the gray value of the current eye image and the gray value projected from the map into the current eye image at the respective coordinate x, y. Summing these gray value differences over all reference image points yields the so-called total gray value difference. Subsequently computer 22 conducts a minimization algorithm in which the degrees of freedom of the eye model, in particular its translation and/or rotation coordinates are varied in such a way as to minimize the total gray value difference.

The set of coordinates obtained then represents the movement of the person's eye 10 which has meanwhile occurred with respect to the reference image. Again, based on this information computer 22 can control laser apparatus 26 via control line 28 such as to compensate for the eye movement and to make sure that laser beam 30 hits the desired spot on cornea 16 or to completely switch off the laser beam 30.

Again, like in the above-discussed embodiment using a feature template map, more than six degrees of freedom of the eye 10 may be taken into account during alignment step S130, in particular relative movements of eye model features, scaling of the whole eye model, scaling of eye model features, deformations of the whole eye model, deformations of eye model features and appearance changes due to illumination influences.

Stated in other words, in all embodiments of the method according to the invention the movement of the eye 10 with respect to its initial position as measured by the reference image is determined by a numerical computer algorithm trying to find the optimum coordinate transformation for the texture information from the coordinate system x', y', z' attached to the eye to the fixed coordinate system x, y, z attached to the camera device in such a way as to minimize the above-defined image distance or the above-defined total gray value difference.

The method according to the invention as well as the corresponding computer program according to the invention are not limited by the above-discussed embodiments which serve for illustrative purposes only. In particular, during the model acquisition phase the reference spatial relationship of the eye shape model with respect to camera device 20 may be obtained by other methods than the above-discussed purkinje analysis. For example, as shown in FIG. 13, the well-known method of triangulation of eye surface points using a projected fringe pattern may be used. In this case, a projecting device 46 is used to direct a light beam onto the surface of the person's eye 10. As a projecting device 46, a laser diode or any other projector may advantageously be used. The fringes in the image taken by camera device 20 are detected and allow to recover depth information at these points by triangulation in order to construct a three-dimensional point cloud of surface points of the exposed eye 10. A three-dimensional model of the eye can then be constructed either by fitting a parametric surface into the three-dimensional point cloud (preferably an ellipsoid, in particular a sphere) or by using the point cloud itself as the reference model.

Figure 14:
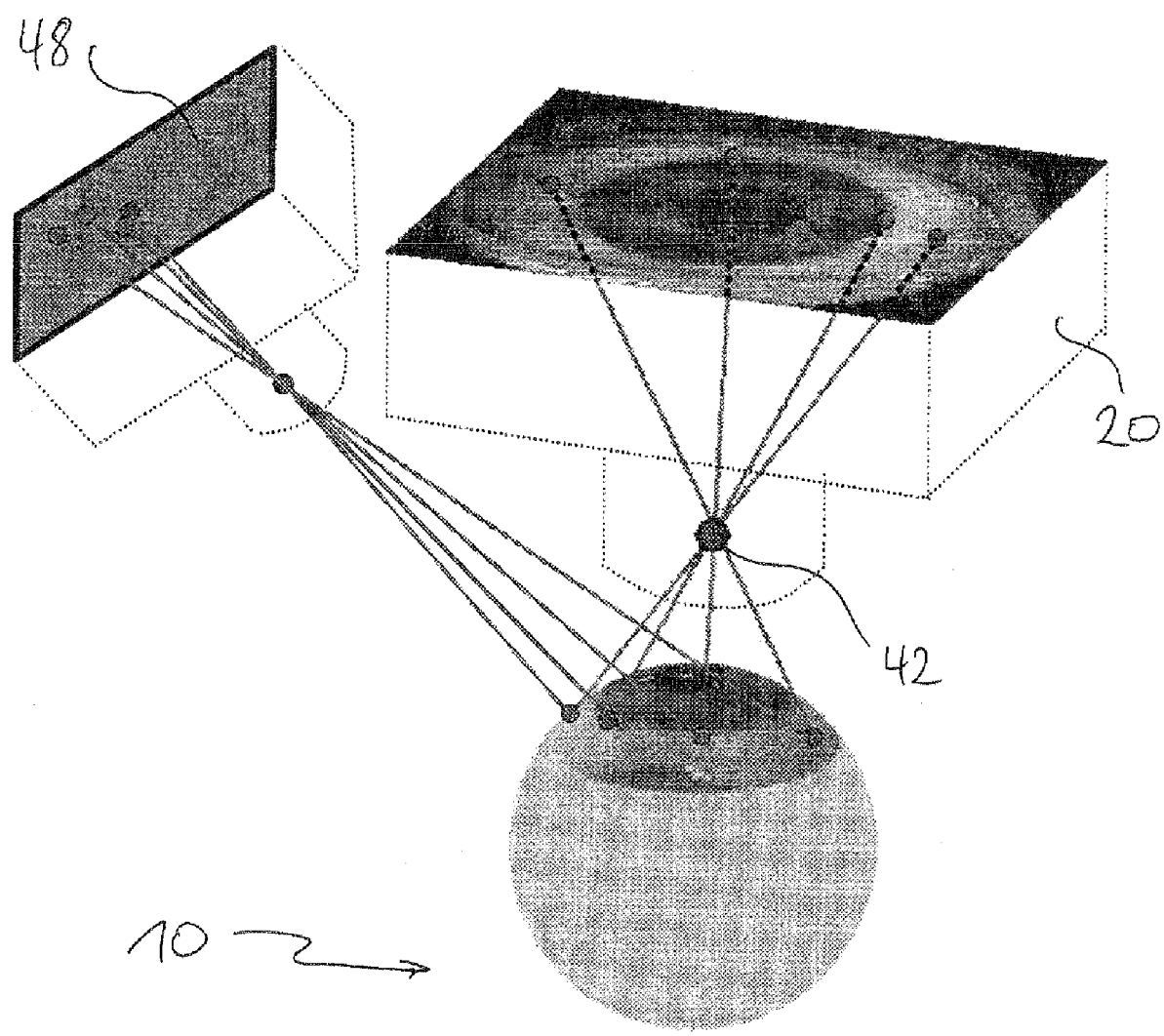
FIG. 14 shows yet another experimental setup used in an alternative embodiment based on eye model acquisition by multiple cameras.

As another alternative shown in FIG. 14, the reference spatial relationship of the eye shape model with respect to camera device 20 may be determined using a further camera device 48. In this case, stereo matching techniques are employed to detect corresponding points in both images, i.e. an image in camera device 20 and a simultaneously taken image in further camera device 48. For these points depth information can be recovered by triangulation in order to construct a three-dimensional point cloud of surface points of the exposed eye. A three-dimensional model of the eye can then be constructed either by fitting a parametric surface into the three-dimensional point cloud (preferably an ellipsoid, in particular a sphere) or by using the point cloud itself as the reference model.

Furthermore it has to be emphasized that the texture information need not necessarily be associated with points located on the surface of the eye. On the contrary, one could also use characteristic visible features of the retina like for example retina blood vessels, the optical nerve head, the fovea or individual features of unhealthy eyes like drusen as characteristic features which are determined and stored in the feature template map. Similarly, the gray value map may be established based on gray values extracted from the reference image of the retina. In this embodiment, however, in which retina information instead of eye surface information is used for tracking purposes, preliminary alignment during the model acquisition phase should also be based on the retina. Therefore, contrary to the above-discussed embodiment in which the three-dimensional eye shape model represents the surface of the eye, in these retina embodiments the three-dimensional eye shape model has to represent the back of the eyeball 12 where the retina is located. Instead of using the above-discussed purkinje analysis, the reference spatial relationship of the eye shape model with respect to the camera device will then usually be obtained by assuming that the person is fixating at a fixed position in space, in particular directly looking at the camera device 20.

In all of its embodiments, the method according to the invention, contrary to prior art techniques, allows to continuously determine all translation and rotation coordinates of the eye 10 without requiring that the cornea 16 remains intact during the tracking phase. Another advantage of the invention is the fact that it can deal with pupil center shifts without introducing systematic errors. When the size of the pupil changes, in particular due to changes in illumination, the center of the pupil shifts with respect to the globe 12. In prior art techniques which rely on localizing the pupil center in the camera image, this leads to systematic errors. In contrast hereto, the method according to the invention is not affected by a shift of the pupil.

The invention claimed is:

1. A method of determining the spatial relationship of an eye of a person with respect to a camera device which provides images of the eye, the method comprising:

in a model acquisition phase:

constructing a three-dimensional shaped customized model of the eye representing the surface of the eye and having texture information associated with a plurality of points located on the surface of the eye, the texture information stored as a feature template map including three-dimensional model coordinates of a plurality of reference image points at which eye features are located, and the feature template map having templates containing parts of the reference image extracted around each associated point and showing the corresponding eye feature, determining a reference spatial relationship of the eye model with respect to the camera device using a reference image of the eye, and aligning the eye shaped model to the reference image of the eye; and in a tracking phase:

determining position and/or rotation coordinates of the eye by aligning the eye model to a current image of the eye, and performing:

a) a template matching step in which, for a plurality of feature templates stored in the feature template map, a region in the current eye image bearing the largest resemblance to the respective feature template is searched;

b) a coordinate determination step in which the coordinates of the regions found in step a) are determined as respective current feature positions; and c) an alignment step in which an image distance between the current feature positions determined in step b) and the positions of the corresponding three-dimensional model features projected into the current eye image is minimized by fitting position and/or rotation parameters of the eye model.

2. The method according to claim 1, in which the three-dimensional eye shape model comprises a superposition of two ellipsoids, one of which represents the globe and the other of which represents the cornea.

3. The method according to claim 2, in which at least one of the two ellipsoids is a sphere.

4. The method according to claim 1, in which the three-dimensional eye shape model comprises a wire mesh structure of connected points.

5. The method according to claim 1, in which the three-dimensional eye shape model comprises a plurality of points defined by linear combinations of shape eigenvectors.

6. The method according to claim 1, in which the reference spatial relationship of the eye shape model with respect to the camera device is obtained by applying a purkinje analysis to the reference image of the eye based on corneal reflexes of illumination sources located at predefined positions relative to the camera device.

7. The method according to claim 1, in which the reference spatial relationship of the eye shape model with respect to the camera device is obtained by assuming that the person is fixating at a fixed position in space previously defined relative to the camera device.

8. The method according to claim 1, in which the features are selected from the group consisting of blood vessels, iris features, limbus, limbus centre, pupil centre, pupil edge and artificial markers.

9. The method according to claim 1, in which the three-dimensional model coordinates of a point are obtained by detecting the corresponding eye feature in the reference image of the eye and intersecting a projecting ray of the eye feature with the aligned eye shape model.

10. The method according to claim 1, in which, for each feature template stored in the feature template map, the search conducted during the template matching step is limited to a predefined zone of the current eye image around the feature position determined in a previous coordinate determination step.

11. The method according to claim 1, in which the tracking phase is continuously repeated in regular time intervals.

12. The method according to claim 1, further comprising determining a spatial relationship of the person's eye with respect to a surgical device based on a previously determined spatial relationship of the camera device with respect to the surgical device.

13. The method according to claim 1, further comprising determining internal degrees of freedom of the eye model selected from the group consisting of relative movements of eye model features, scaling of the whole eye model, scaling of eye model features, deformations of the whole eye model, deformations of eye model features and appearance changes due to illumination influences.

14. A method of determining the spatial relationship of an eye of a person with respect to a camera device which provides images of the eye, the method comprising:

in a model acquisition phase:
constructing a three-dimensional eye shaped customized model of the eye representing the surface of the eye and having texture information associated with a plurality of points located on the surface of the eye, the texture information is stored as a grey value map including: three-dimensional model coordinates of a plurality of previously defined reference image points; and grey values extracted from the reference image at each of the points,
determining a reference spatial relationship of the eye model with respect to the camera device using a reference image of the eye, and
aligning the eye shaped model to the reference image of the eye; and in a tracking phase:
determining position and/or rotation coordinates of the eye by aligning the eye model to a current image of the eye.

15. The method according to claim 14, in which the three-dimensional model coordinates of a point are obtained by intersecting a projecting ray of the reference image point with the aligned eye shape model.

16. The method according to claim 14, in which the tracking phase comprises an alignment step in which the total grey value difference between the current eye image and the grey value map projected into the current eye image is minimized by fitting orientation and/or rotation parameters of the eye model.

17. The method according to claim 14 in which the tracking phase is continuously repeated in regular time intervals.

18. The method according to claim 14, further comprising determining a spatial relationship of the person's eye with respect to a surgical device based on a previously determined spatial relationship of the camera device with respect to the surgical device.

19. The method according to claim 14, further comprising determining internal degrees of freedom of the eye model selected from the group consisting of relative movements of eye model features, scaling of the whole eye model, scaling of eye model features, deformations of the whole eye model, deformations of eye model features and appearance changes due to illumination influences.

20. A computer program, comprising:
computer program code which, when executed on a computer connected to a camera device, enables the computer to carry out a method including:
in a model acquisition phase:
constructing a three-dimensional shaped customized model of the eye representing the surface of the eye and having texture information associated with a plurality of points located on the surface of the eye, the texture information stored as a feature template map including three-dimensional model coordinates of a plurality of reference image points at which eye features are located, and the feature template map having templates containing parts of the reference image extracted around each associated point and showing the corresponding eye feature,
determining a reference spatial relationship of the eye model with respect to the camera device using a reference image of the eye, and
aligning the eye shaped model to the reference image of the eye; and in a tracking phase:
determining position and/or rotation coordinates of the eye by aligning the eye model to a current image of the eye, and
performing:
a) a template matching step in which, for a plurality of feature templates stored in the feature template map, a region in the current eye image bearing the largest resemblance to the respective feature template is searched;
b) a coordinate determination step in which the coordinates of the regions found in step a) are determined as respective current feature positions; and
c) an alignment step in which an image distance between the current feature positions determined in step b) and the positions of the corresponding three-dimensional model features projected into the current eye image is minimized by fitting position and/or rotation parameters of the eye model.

21. A computer program, comprising computer program code which, when executed on a computer connected to a camera device, enables the computer to carry out a method including:

in a model acquisition phase:

constructing a three-dimensional eye shaped customized model of the eye representing the surface of the eye and having texture information associated with a plurality of points located on the surface of the eye, the texture information is stored as a grey value map including: three-dimensional model coordinates of a plurality of previously defined reference image points and grey values extracted from the reference image at each of the points, determining a reference spatial relationship of the eye model with respect to the camera device using a reference image of the eye, and aligning the eye shaped model to the reference image of the eye; and in a tracking phase:

determining position and/or rotation coordinates of the eye by aligning the eye model to a current image of the eye.

* * * * *